United States Patent [19]

Wu

[11] Patent Number: 5,592,690

[45] Date of Patent: *Jan. 14, 1997

[54] ELASTIC LAMINATED SHEET FOR ARTICLES OF CLOTHING

[75] Inventor: Pai-Chuan Wu, Cincinnati, Ohio

[73] Assignee: Clopay Plastic Products Company, Inc., Cincinnati, Ohio

[*] Notice: The term of this patent shall not extend beyond the expiration date of Pat. No. 5,422,172.

[21] Appl. No.: 346,884

[22] Filed: Nov. 30, 1994

Related U.S. Application Data

[63] Continuation-in-part of Ser. No. 104,791, Aug. 11, 1993, Pat. No. 5,422,172.

[51] Int. Cl.[6] .................................................. D03D 17/00
[52] U.S. Cl. .......................... 2/67; 2/113; 2/211; 2/221; 2/401; 2/237; 2/239; 428/230; 428/231; 428/486; 428/487
[58] Field of Search .................................. 428/230, 231, 428/286, 287; 2/67, 113, 211, 221, 401, 237, 239

[56] References Cited

U.S. PATENT DOCUMENTS

| | | | |
|---|---|---|---|
| 2,714,571 | 8/1955 | Irion et al. | 154/139 |
| 3,058,868 | 10/1962 | Palatine, III | 156/153 |
| 3,622,421 | 11/1971 | Newmann | 156/306 |
| 3,868,729 | 3/1975 | Lynam | 428/230 X |
| 4,107,364 | 8/1978 | Sisson | 428/196 |
| 4,153,664 | 5/1979 | Sabee | 264/289 |
| 4,366,814 | 1/1983 | Riedel | 428/230 X |
| 4,379,197 | 4/1983 | Cipriani et al. | 428/220 |
| 4,517,714 | 5/1985 | Sneed et al. | 28/103 |
| 4,522,203 | 6/1985 | Mays | 128/132 |
| 4,525,407 | 6/1985 | Ness | 428/138 |
| 4,614,679 | 9/1986 | Farrington, Jr. | 428/138 |
| 4,673,615 | 6/1987 | Murphy, et al. | 428/286 |
| 4,692,368 | 9/1987 | Taylor et al. | 428/137 |
| 4,725,473 | 2/1988 | Gompel et al. | 428/156 |
| 4,753,840 | 6/1988 | Gompel | 428/171 |
| 4,761,324 | 8/1988 | Rautenberg et al. | 428/230 X |
| 4,834,741 | 5/1989 | Sabee | 604/385.2 |
| 4,981,747 | 1/1991 | Mormon | 428/198 |
| 5,035,941 | 7/1991 | Blackburn | 428/286 |
| 5,049,426 | 9/1991 | Kinura et al. | 428/230 X |
| 5,143,679 | 9/1992 | Weber et al. | 264/288.8 |
| 5,151,092 | 9/1992 | Buell et al. | 604/385.2 |
| 5,156,793 | 10/1992 | Buell et al. | 264/288.8 |
| 5,156,897 | 12/1992 | Weber et al. | 264/288.8 |
| 5,221,572 | 6/1993 | Meunier | 428/231 |
| 5,236,430 | 8/1993 | Bridges | 604/396 |

FOREIGN PATENT DOCUMENTS

| | | |
|---|---|---|
| 0187725 | 7/1986 | European Pat. Off. . |
| 9215444 | 9/1992 | WIPO . |

*Primary Examiner*—Jenna Davis
*Attorney, Agent, or Firm*—Wood, Herron & Evans, P.L.L.

[57] ABSTRACT

Clothing garments and other articles include an elastic laminated sheet having the properties of stretchability and recoverability. The elastic laminated sheet is formed from a nonwoven fibrous web and an elastomeric film laminated to at least one entire web surface. The laminate is incrementally stretched along lines substantially uniformly across its length and width and throughout its depth to form a stretchable and recoverable composite. The elastic laminated sheet is uniquely suited for use in athletic and active wear garments. The composite is also useful for single use or throw away clothing articles such as medical or surgical garments, throw away bathing suits, underpants, undershirts, and garments used in the handling of hazardous or waste materials.

9 Claims, 1 Drawing Sheet

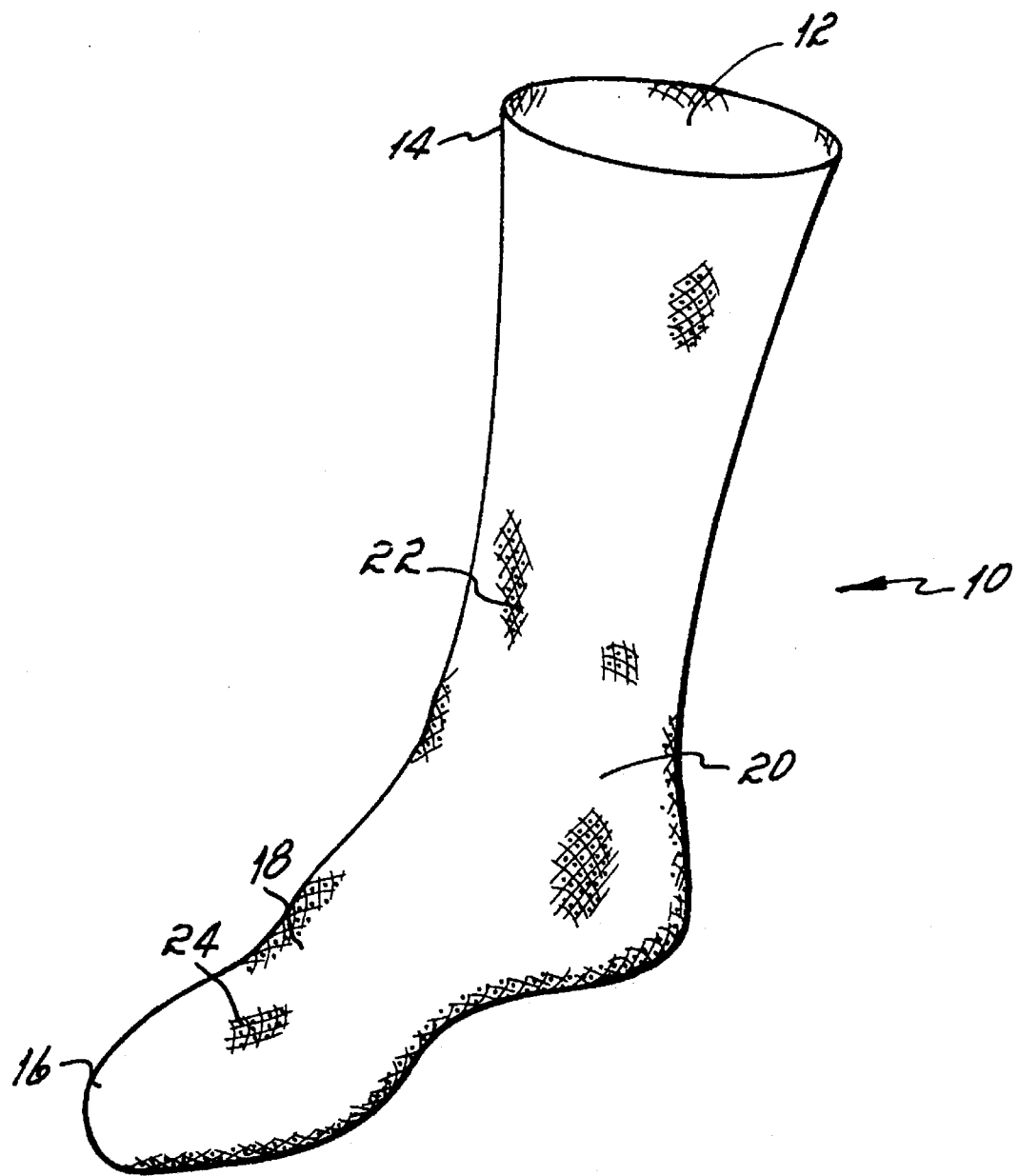

ELASTIC LAMINATED SHEET FOR ARTICLES OF CLOTHING

This application is a continuation-in-part of application Ser. No. 08/104,791, now U.S. Pat. No. 5,422,172, filed Aug. 11, 1993.

FIELD OF THE INVENTION

The present invention relates to an improved elastic laminated sheet for use in articles of clothing, and more particularly, to an elastic laminated sheet which allows for the stretching and recovery of articles of clothing in response to movements of a wearer.

BACKGROUND OF THE INVENTION

Articles of clothing and single use garments are commonly used in a variety of areas such as athletic and active wear, surgical and medical applications, waste or hazardous material handling, and "throw-away" bathing suits or undergarments. Single use garments are those which are worn or used by an individual once, or a limited number of times, and then discarded. Both single use garments and other articles of clothing should be inexpensive to manufacture while remaining comfortable for the wearer. Comfort is a prime consideration for articles of clothing, but the cost of manufacturing single use items and other articles of clothing is also an important criteria in that increased costs can prove to be prohibitive to the successful commercialization of such a product.

Comfort is an important criteria in that articles of clothing are very often worn or used directly in contact with the individual's skin or body. Comfortable articles of clothing should be both soft, so as not to irritate the skin of a wearer, and be stretchable and recoverable, so as not to constrain or bind during movement by the wearer. Stretchability and recoverability are particularly desirable for active and athletic wear so that the wearer is not constrained or restricted and the fabric does not rip or bind during wear and/or movement.

As a result of the requirements of comfort and economy, nonwoven thermoplastic films are commonly used in the production of disposable absorbent articles such as diapers, catamenial pads, and incontinent articles. To achieve the desired qualities, thermoplastic films are often laminated or bonded to other nonwoven materials.

Processes of bonding nonwoven fibrous webs to thermoplastic films have been known for sometime. Additionally, methods for extrusion laminating of thermoplastic films to unstretched nonwoven webs are well-known in the art. Extrusion lamination of unstretched nonwoven webs entails stretching extruded polymeric films prior to laminating with unstretched nonwoven fibrous webs at the nips of a pressure roller. Other methods of extrusion lamination include coextruding multiple polymeric films with unstretched nonwoven webs at the pressure roller nips. One method of improving the bonding between nonwoven fibers and thermoplastic films is to preform the nonwoven polymeric fiber materials prior to extrusion lamination with the thermoplastic films.

It has also been known to stretch nonwoven fibrous webs using intermeshing rollers to reduce the weight of the nonwoven sheet for use in disposable or single use articles. Methods of stretching nonwoven fibrous webs include incremental cross direction or machine direction stretching with a pair of interdigitating rollers to strengthen and soften the nonwoven webs and thereby provide a more desirable material for single use articles. Techniques for bonding nonwoven fibrous webs to thermoplastic films and patents directed thereto are fully disclosed in the above identified application, Ser. No. 08/104,791, filed Aug. 11, 1993, which is incorporated herein by reference. However, even though it is known to bond nonwoven fibrous webs to thermoplastic films to produce a more desirable laminate, the films up to now have been bonded to only limited portions of the web resulting in an improved laminate for only a patch or discrete area of the product.

There is a continuing need for improved laminates of nonwoven fibrous substrates in plastic films that provide sufficient qualities such as softness, comfort, and economical manufacturing for use in articles of clothing. It would be very desirable to further improve the properties of such laminates and to expand their utility in articles of clothing and other useful products to provide the properties of stretchability and recoverability.

SUMMARY OF THE INVENTION

This invention is directed to articles of clothing, active wear and athletic clothing which include an elastic laminated sheet of a nonwoven fibrous web and an elastomeric film. The term "elastic" is used in the specification and claims as meaning stretchable under force and recoverable to its original or essentially original form upon release of that force. The fibrous web has a multitude of fibers extending outwardly from the laminated surface that are formed by incremental stretching of the laminated sheet along lines substantially uniform across the laminated sheet and throughout its depth. The laminated elastomeric film is stretchable and recoverable to provide elasticity to the entire laminated sheet instead of just discrete patches and thereby offer a more comfortable article of clothing which is capable of responding to the movements of the wearer.

This invention provides for articles of clothing which include laminates of nonwoven fibrous substrates and elastomeric films that have sufficient softness so as not to irritate the skin of a wearer, but which are coupled with the properties of stretchability and recoverability over the entire laminate to respond to movement by the wearer. In addition, the elastic laminate can be produced economically on high speed production machinery. The elastic laminated sheet of this invention is ideally suited for articles of clothing and other personal use products where stretchability and recoverability are significant properties. Such articles include shirts, pants, skirts, dresses, socks, athletic wear, swimsuits, shorts, medical and/or surgical garments, and waste or hazardous material handling garments. The elastic laminated sheet can be included as the primary or major component of these articles where the properties of stretchability and recoverability are desirable. Stretchability and recoverability offer a garment or article of clothing the ability to respond to the movements of a wearer as opposed to restricting movement or tearing, rupturing or breaking as a result thereof. Previously, stretchability and recoverability were imparted to only specific patches of the article where the film was bonded to the web which would be insufficient for use of the laminated sheet in an article of clothing or for athletic and active wear.

The elastic laminated sheet comprises a nonwoven fibrous web and an elastomeric film laminated to at least one entire web surface. The elastomeric film may be on one side of the nonwoven or between the nonwovens to form the elastic laminate. The laminate is incrementally stretched along lines substantially uniformly across its length and width and throughout its depth to form a stretchable and recoverable composite sheet. Elasticity in the composite sheet is mainly attributable to the elastic film. Under elongation or deformation forces, the laminate is stretchable and thus would conform, for example, to parts of the body when employed in an article of clothing as previously described. Similarly, with the unique property of elastic recovery, the laminate will essentially return to its original state. Furthermore, the properties of stretchability and recoverability are not limited to only patches or discrete areas of the sheet, but across the entire surface area. As a result, the comfort and ability to accommodate the movements of a wearer are not limited to specific patches, regions or areas of the garment. The laminate may be repeatedly subjected to stretching and recovery without significant degradation in these properties to thereby provide a durable material for repeated stretching and use in such articles.

In a preferred form, the elastic laminated sheet employs an elastomeric film having a gauge or a thickness between about 0.25 and 10 mils and, depending upon use, the film thickness will vary and, most preferably, is on the order of about 0.25 to 2 mils in thickness. The nonwoven fibrous webs of the laminated sheet normally have a weight of about 10 grams per square yard to 60 grams per square yard and preferably about 20 to about 40 grams per square yard. When employing adhesive lamination, adhesives such as hot melt adhesive, water base adhesive or solid base adhesive may be used. As used herein, "nonwoven fibrous web" is used in its generic sense to define a generally planar structure that is relatively flat, flexible and porous, and is composed of stable fibers or continuous filaments.

The laminated sheet is incrementally stretched along lines substantially uniform across the laminate and throughout its depth to provide an elastic laminated sheet. By applying an incremental stretching force to the laminated sheet, both the web and film are stretched. Upon removing the stretching force from the laminated sheet, the elastic film recovers its shape and fibers of the web are thereby caused to extend outwardly from the bond web surface to give loft and enhanced softness to the laminated sheet.

The permanent set of the elastic laminate employed in this invention is no more than approximately 10% of its original dimension after first stretching to about 50% of its original shape. "Permanent set" means the final unrecoverable dimension of the composite after being stretched.

The elastomeric film recovers its original or substantially original shape after stretching, whereas the web after stretching will increase in thickness and softness. This is one of the unique features of the laminate thereby making it particularly suited for use in articles of clothing and athletic wear. The softness of the web resulting from the stretching and recovering is uniquely advantageous for the use of this laminate in articles of clothing and items used against the skin. The repeated stretching and rubbing of the laminate against the skin will not cause irritation and discomfort as with other materials previously known in the art but will produce a soft and comfortable interface with the wearer.

The elastic laminate employed in this invention in one presently preferred form is characterized by being impervious to the passage of fluid by virtue of the elastomeric film while maintaining the softness, stretchability and recoverability of the entire area of the laminate. The liquid imperviability of the laminate sheet is particularly useful in hazardous or waste material handling garments to prevent penetration of contaminants through to the wearer's skin or in surgical gowns and hospital wear.

Alternatively, various degrees of vapor or air permeability may be achieved in the elastic laminated sheet while providing mechanical microvoids or perforations, for instance. With the microvoids or perforations introduced into the elastic laminated sheet, the laminate can provide the permeability, softness, stretchability and recoverability properties needed for athletic and active wear. The breathability of such articles is advantageous to help dissipate the wearer's perspiration or other moisture.

The above features and advantages of this invention will be better understood in reference to the accompanying figure, detailed description, and previously identified application, Ser. No. 08/104,791, which is incorporated herein by reference. It should also be understood that the particular materials of the laminated sheet, articles of clothing, garments, personal use items, and other articles identified herein are exemplary only and are not to be regarded as limitations of the invention.

BRIEF DESCRIPTION OF THE DRAWING

Reference is now made to the accompanying FIGURE from which the novel features and advantages of the present invention will be apparent. The FIGURE is a perspective view of an article of clothing, namely a sock, made from an elastic laminated sheet, of the present invention.

DETAILED DESCRIPTION OF THE INVENTION

By way of illustrating and providing a more complete appreciation of the present invention and many of the attendant advantages thereof, the following detailed description is given concerning the novel elastic laminated sheet properties, articles made therewith, and methods of production and use thereof.

Although the detailed description given herein is directed to a sock, this physical embodiment is intended to merely exemplify the present invention which may be employed in other applications, such as articles of clothing, athletic wear, active wear and other garments. Specifically, the elastic laminated sheet of this invention is particularly advantageous for economical and comfortable use in shirts, dresses, skirts, pants, socks, shorts, and portions thereof at the intersection of a wearer's limbs and torso or other joints. Limb, joint and torso movement will not be restricted or confined by the stretchable and recoverable properties of this invention, nor will skin irritation likely develop as a result of contact with the material of this invention due to the softness thereof.

As used herein, the term "article of clothing" refers to articles which are worn by a person. More specifically, these articles are placed either against or are in proximity to the body of the user or worn over and/or in combination with other articles. They may be intended to be discarded after a single use or used repeatedly.

A preferred embodiment of the present invention is shown in the figure as a sock 10. Although the present invention is shown and described herein with reference to a sock, it should be understood that this invention is also applicable to other articles of clothing.

The sock 10 is fabricated to have a generally tubular configuration or a configuration more closely resembling the shape of the human foot as shown in the FIGURE. The sock includes an open uppermost end 12 and an adjacent cuff region 14. The sock 10 also includes a lower closed end 16. In use, while being worn on the foot of a wearer, the cuff region 14 surrounds the wearer's calf (not shown) whereas the closed end region 16 covers the wearer's toes (not shown). Adjacent to the closed end 16 of the sock are a foot portion 18 and an ankle and heel portion 20. Adjacent to the ankle portion 20 is a lower calf portion 22 of the sock 10 just below the cuff region 14.

The sock 10 or other article of clothing fabricated from the elastic laminated sheet of this invention is both stretchable and recoverable to provide a more comfortable article of clothing.

In a preferred embodiment of this invention, the elastic laminated sheet includes an increased elastic portion at the cuff 14 of the sock 10 to provide a tighter fit around the wearer's calf and to minimize the tendency for the sock 10 to fall or sag toward the ankle (not shown) of the wearer.

Preferably, the enhanced stretchability and elastic region provided at the cuff 14 of the sock 10 is in a circumferential direction in addition to the multi-directional stretchability and recoverability of the underlying laminate itself. The enhanced elastic property imparted to the cuff region 14 in a circumferential direction aids in holding the sock 10 around the wearer's calf.

Furthermore, the elastic laminated sheet and article of clothing are more durable and are less likely to tear or rip in response to the movements of the user. Particularly, movements such as walking, running, stressing or flexing of the foot will not cause the sock 10 according to this invention to tear or rip in that the elastic laminated sheet stretches with movements of the wearer and recovers to substantially its original configuration. An additional advantageous feature of the sock 10 or other article of clothing manufactured according to this invention is the web of the laminate after stretching will increase in thickness and softness. The softness of the web resulting from the stretching and recovering of the laminate because of repeated movement by the wearer will not cause irritation and rubbing of the skin in the regions adjacent to the sock 10 or other article of clothing. As a result, articles of clothing according to this invention are uniquely comfortable to wear and become increasingly so through use and movement by the wearer.

In a presently preferred form of the sock 10 or other article of clothing according to this invention, vapor or air permeability is imparted to the elastic laminate material by providing mechanical microvoids or perforations 24. The microvoids or perforations introduced into the elastic laminated sheet impart breathability to the sock 10 or other article of clothing which is advantageous to help dissipate the wearer's perspiration, moisture or other such fluids in contact with the article.

The stretchability and recoverability of the elastic laminated sheet is not limited to only a specific patch or area of the laminate as in prior laminates. However, the entire surface area of the laminate has the properties of stretchability and recoverability to afford comfort and durability to the entire sock 10 or other article of clothing and not just to particular regions thereof. Furthermore, the stretchability and recoverability is preferably imparted to the article of clothing in a multi-directional orientation so that movement by the wearer results in the stretching and recovering of the laminate to substantially its original configuration in more than only one direction.

It will be appreciated by one of ordinary skill in the art that the foregoing embodiment incorporating the elastic laminated sheet is exemplary only that this invention can be applied to other articles of clothing, athletic or active wear, garments used in the handling of hazardous or waste materials, surgical or medical garments, and other articles of clothing without deviating from the scope of this invention.

A more complete and detailed description of the elastic laminate sheet and production methods thereof can be found in the above described application Ser. No. 08/104,791 filed Aug. 11, 1993, incorporated herein by reference.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof.

We claim:

1. An article of clothing selected from the group consisting of a shirt, a pant, a skirt, a dress, an undergarment and a sock, the article of clothing including an elastic laminated sheet proximate a joint of a wearer, said sheet comprising an elastomeric film and a nonwoven fibrous web laminated to substantially a surface of said film to form said laminated sheet, said laminated sheet having a multitude of fibers extending outwardly from said laminated surface, said fibers being formed by incrementally stretching of the laminated sheet along lines substantially uniformly across the laminated sheet and throughout its depth, said laminated sheet being stretchable and recoverable in response to movements of the joint of the wearer to provide a more comfortable and durable article of clothing, said laminated sheet having a permanent set after being stretched to 50% of its original shape of no more than about 10%.

2. The article of claim 1 wherein said fibrous web comprises fibers selected from the group consisting of polypropylene, polyethylene, polyester, cellulose, rayon, nylon and blends of two or more of such fibers and the polymer of said elastomeric film is selected from the group consisting of poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), and ethylene-propylene rubber and said film has a thickness on the order of about 0.25 mils to about 10 mils.

3. The article of claim 2 wherein said nonwoven fibrous web has a weight of about 10 grams/square yard to about 60 grams/square yard.

4. The article of claim 2 wherein said elastomeric film has a thickness on the order of about 0.25 mils to about 2 mils and the nonwoven fibrous web has a weight on the order of about 20 grams/square yard to about 40 grams/square yard.

5. The article of claim 1 wherein said elastic laminated sheet is incrementally stretched in a cross direction to form a stretchable and recoverable composite in said cross direction.

6. The article of claim 1 wherein said elastic laminated sheet is incrementally stretched in both its cross direction and longitudinal direction to form a stretchable and recoverable composite which is stretchable and recoverable in both said cross and longitudinal directions.

7. The article of claim 1 wherein said elastomeric film has opposite surfaces and a nonwoven fibrous web is laminated to both surfaces to provide said laminated sheet.

8. The article of claim 1 wherein the article is selected from the group consisting of a sock, a pair of athletic shorts, a pair of athletic pants, a bathing suit, an underpant, an undershirt, a single-use garment, a medical gown, a surgical pant, and a surgical shirt.

9. The article of claim 1 wherein at least a portion of elastic laminated includes microvoids to permit the passage of fluids therethrough.

* * * * *